US00PP10013P

United States Patent [19]

Osiecki

[11] Patent Number: Plant 10,013

[45] Date of Patent: Aug. 26, 1997

[54] SPATHIPHYLLUM PLANT 'S4'

[75] Inventor: Marian W. Osiecki, Marianna, Fla.

[73] Assignee: Oglesby Plant Laboratories, Inc., Altha, Fla.

[21] Appl. No.: 638,139

[22] Filed: Apr. 26, 1996

[51] Int. Cl.[6] ..... A01H 5/00

[52] U.S. Cl. ..... Plt./88.1

[58] Field of Search ..... Plt./88.1

*Primary Examiner*—James R. Feyrer
*Assistant Examiner*—Kent L. Bell
*Attorney, Agent, or Firm*—Rothwell, Figg, Ernst & Kurz, pc

[57] ABSTRACT

A new and distinct cultivar of Spathiphyllum is provided. The plant is medium size, full, suitable for production in a 15–20 cm pot from a single tissue culture produced microcutting; grows vigorously; has early, abundant branching and dark green foliage. Natural flowering is early, abundant and year-round. Long-lasting spathes of unique shape and good quality from the onset of flowering are held on strong, straight peduncles.

2 Drawing Sheets

SUMMARY OF THE INVENTION

This invention relates to a new and distinct Spathiphyllum cultivar characterized by the following combination of repeatedly observed traits:

1. Medium size,
2. full growth habit,
3. vigorous growth,
4. early and abundant branching,
5. early, abundant and year-round natural flowering,
6. dark green, glossy foliage,
7. unique spathe shape,
8. good inflorescence quality from the onset of flowering;

and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Oglesby Plant Laboratories, Inc. near Altha, Fla. The female parent was a selected clone of Spathiphyllum 'Starlight' and the male parent was a selected clone of Spathiphyllum 'Petite'. The cross was made in 1991, the plant was selected in 1992 and has since been reproduced by tissue culture in the vicinity of Altha, Fla. with the characteristics stated, found to be maintained through successive generations.

This new cultivar has been identified as Spathiphyllum 'S4'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S4' was approximately 17 months from planting a single tissue culture produced microcutting and was grown in a 20 cm pot.

In the photographs:

DETAILED DESCRIPTION OF THE NEW CULTIVAR

Figure 1:
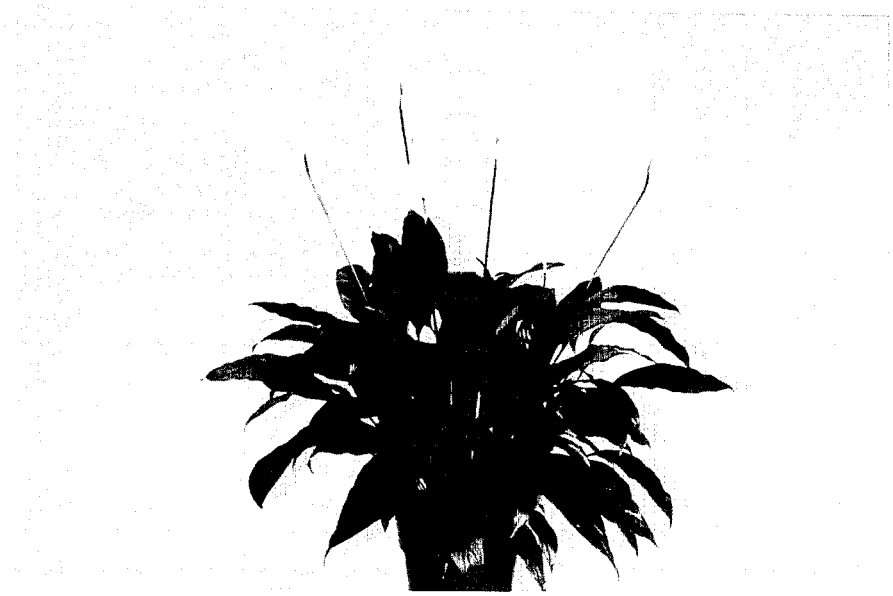
FIG. 1 depicts the whole plant.
Figure 2:
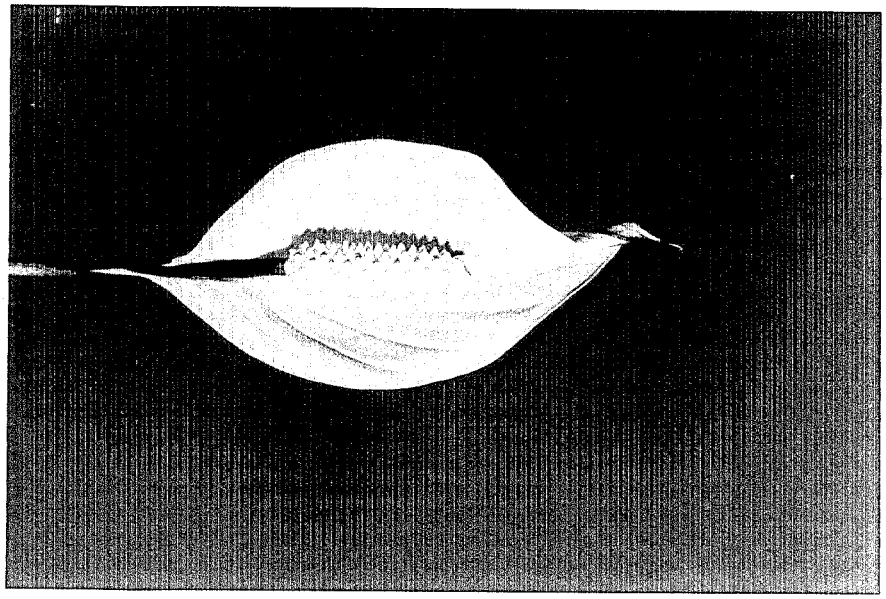
FIG. 2 illustrates the mature inflorescence.
Figure 3:
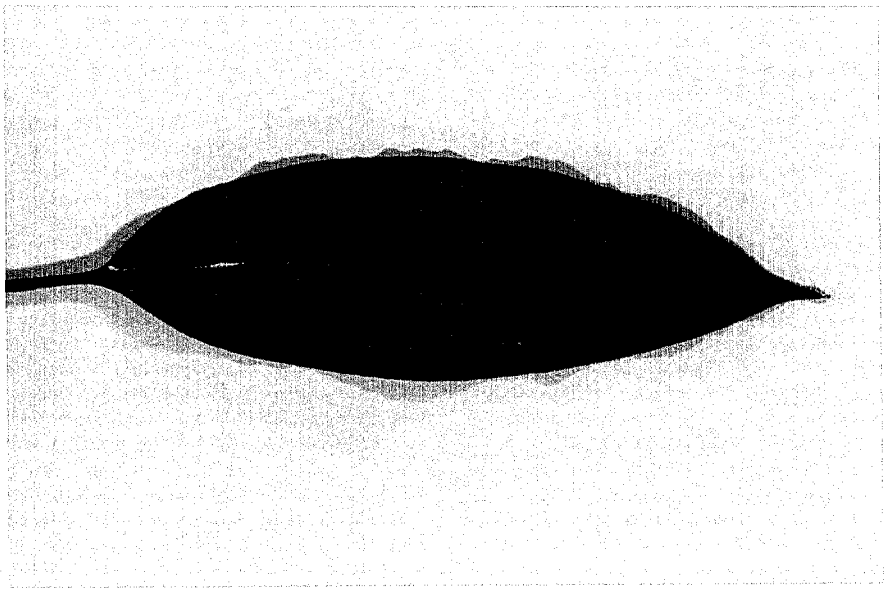
FIG. 3 illustrates the top of a mature leaf.
Figure 4:
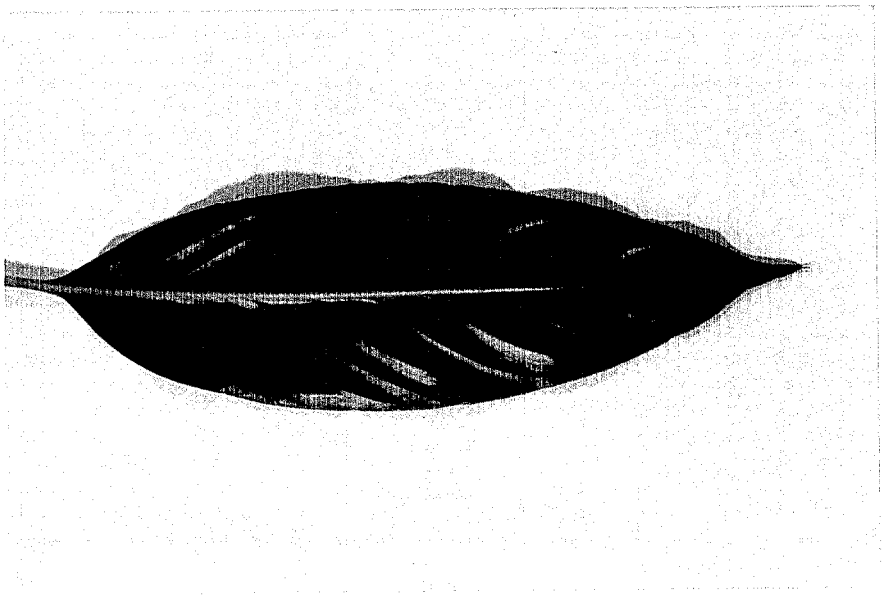
FIG. 4 illustrates the bottom of a mature leaf.

The following observations and measurements describe plants grown near Altha, Fla. under greenhouse conditions. These observations and measurements were recorded in December, 1994 from mature plants (about 14.5 months from planting tissue cultured microcuttings) grown in 20 cm pots. Fully developed organs were used for measurements. Color values were determined on Dec. 27, 1994, under a mixture of natural, indirect light and artificial light, totaling approximately 270 foot-candles. Color references are made to The R.H.S. Color Chart, except where general color terms of ordinary significance are used.

'S4' has not been observed under all possible environmental conditions. The phenotype may vary with variations in environment and horticultural practices, such as temperature, light intensity, day length, fertilization, propagation method, etc., without any change in genotype.

Parentage:

*Female parent.*—Selected clone of Spathiphyllum 'Starlight'.

*Male parent.*—Selected clone of Spathiphyllum 'Petite'.

Propagation: Plant tissue culture.

Plant:

*Growth habit.*—Medium size, full, very well branched, relatively upright.

*Height.*—Foliage 35–47 cm, with spathes 56–71 cm.

*Maximum width.*—6–72 cm.

Petiole:

*Size.*—18–28.5 cm long, 2.0–3.0 mm in diameter (immediately below geniculum).

*Geniculum.*3.2–4.4 cm long, 2.5–4.0 mm in diameter; not very conspicuous.

Leaf blade:

*Shape.*—Narrowly elliptic to lanceolate; leaves supporting inflorescences usually less elongated than other leaves of similar age; width divided slightly unequally by midrib; tip—acuminate, usually slightly curving downwards and/or sometimes to the side; base—cuneate, narrowly decurrent on peduncle; margin slightly wavy.

*Size.*—Leaf supporting inflorescence: 18.4–23.0 cm long by 6.0–8.2 cm wide; length:width ratio 2.6–3.2:1. Leaf penultimate to leaf supporting inflorescence: 20.5–22.0 cm long by 6.1–7.6 cm wide; length:width ratio 2.8–3.5:1.

*Texture.*—Smooth, glossy; young leaves hightly polished.

*Veins.*—Well defined and sunken.

*Color.*—Mature leaf: Adaxial: darker than 147 A (yellow-green). Abaxial: between 147 A and 147 B (yellow-green). Young leaf: Adaxial: between 146 A (yellow-green) and 137 A–B (green). Abaxial: 147 B (yellow-green).

Inflorescence:

*Arrangement.*—Spathes carries on strong, straight peduncles a moderate distance from the foliage; spadix short in relation to spathe (spathe length:spadix length ratio 2.7–3.4:1).

*Development.*—When spathe opens spadix and spathe are slightly leaning forward. They retain this position through senescence or become more vertical. Frequently spadix is appressed or nearly appressed against midrib through senescence.

Peduncle:

*Size.*—43.5–57.8 cm long, 3.5–5.5 mm in diameter (below spathe). A bump on back side marks the base of stipe; 5–7 cm long section immediately below spathe is slightly thicker than lower portion, but on most peduncles the thickening is negligible.

*Color.*—(*immediately below spathe*).—Front: between 143 A (green), 137 D (green) and 144 A (yellow-green). Back: 143 A (green).

*Stipe.*0.5–0.8 cm long, 3.0–4.5 mm in diameter.

Spathe:

*Shape.*—Elliptic, cupped through senescence; in the distal portion it remains partially rolled and twisted through senescence; tip—acuminate, twisted; base cuneate, variably asymmetric.

*Size.*—10.5–14.5 cm long by 3.9–6.2 cm wide and 1.5–2.2 cm deep; length:width ratio 2.4–2.7:1.

*Color.*—155 D (white) with some green coloration on back side; very small amount of green on front side of the tip usually hidden by its twist. The green on back side is a stripe continuing from the peduncle and tapering to less than 1 mm approximately at the middle of spathe's length. In the proximal half the center of the stripe is green (137 C, 138 A) and the margins are a little darker (137 A-B). There is a little light spot (between 144 A-B-yellow-green and 143 C-green) immediately below the bump marking the base of the stipe. Narrow midrib in the distal half of the spathe is yellow-green (144 A-B), except for the tip, where it becomes a little darker (137 A-green). Most of the tip on both sides of midrib is occupied by diffused yellow-green (144 A). Most lateral veins, especially close to midrib, are green (143 B-C).

Spadix:

*Size.*—3.1–5.3 cm long; 1.1–1.4 cm in diameter.

*Color.*—pistils 158 A-B, perianth 158 C (both yellow-white).

Botanical flower:

*Perianth.*—Well visible between relatively thin pistils, segments united.

*Pistil.*—Relatively thin, acute, extrudes approximately 1.5–2 mm beyond perianth; stigma minute (not visible with naked eye).

*Stamens.*—Not visible before pollen release.

Flowering: Continuous year-round flowering in 15 cm pots begins about 8–10 months from planting tissue culture produced microcuttings; after approximately 14 months two to seven white spathes constantly present above foliage.

Spathe longevity: Spathe remains white for up to 5 weeks following bud appearance above foliage and then gradually changes to a green color.

Roots: Numerous, thin, fleshy white main roots, lateral roots not very abundant.

Disease and insect resistance: No unusual susceptibility to diseases or insects noted to date.

COMPARISON WITH THE KNOWN CULTIVARS

The new cultivar can be compared to the known cultivars: 'Bond A' U.S. Plant Pat. No. 8,849 (a/k/a Symphony) and to 'Starlight'. Observations for comparisons were made on plants grown under similar conditions in a greenhouse near Altha, Fla.

'S4' is distinguished from both cultivars by its more vigorous growth; earlier branching; more upright growth habit; earlier, year-round natural flowering; stronger, straighter and longer peduncles; better quality and uniformity of inflorescences; unique shape of spathe and shorter leaf blade tips.

'S4' is further distinguished from 'Starlight' by its more abundant branching and wider leaves.

I claim:

1. A new and distinct cultivar of Spathiphyllum plant named 'S4', substantially as described and illustrated herein, characterized particularly as to novelty by its medium size; vigorous growth; early and abundant branching; early, abundant, year-round natural flowering; good quality inflorescences from the onset of flowering and unique shape of spathes.

* * * * *